(12) United States Patent
Nakano

(10) Patent No.: US 6,486,330 B1
(45) Date of Patent: Nov. 26, 2002

(54) 4-OXATRICYCLO[4.3.1.1 $^{3,8}$]UNDECAN-5-ONE DERIVATIVE AND PROCESS FOR PRODUCING THE SAME

(75) Inventor: Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 38 days.

(21) Appl. No.: 09/648,755

(22) Filed: Aug. 28, 2000

(30) Foreign Application Priority Data

Sep. 1, 1999 (JP) .......................................... 11-248083

(51) Int. Cl.$^7$ ............................................. C07D 313/08
(52) U.S. Cl. ...................................................... 549/270
(58) Field of Search ......................................... 549/270

(56) References Cited

U.S. PATENT DOCUMENTS 6,303,266 B1    10/2001  Okino et al.

FOREIGN PATENT DOCUMENTS

| EP | 0824962 | 2/1998 |
| EP | 0878234 | 11/1998 |
| JP | 08038909 | 2/1996 |

OTHER PUBLICATIONS

I.I. Starovoitov et al., *Doki. Akad. Nauk.*, 1994, pp. 241–244, vol. 334, No. 2; XP–000926090.

J.Hlavaty et al; Sbornik Vysoke Skolny Chemicko–Technologicke V Praze, Technologie Paliv; vol. D49, 1984, pp. 205–215; XP–000926089.

S.A. Selifonov; Biochemical and Biophysical Research Communications; vol. 186, No. 3, (Aug. 14, 1992); pp. 1429–1436; XP–000961092.

H. Suginome et al; Synthesis; Sep. 1986; pp. 741–743; XP–000961094.

*Primary Examiner*—T. A. Solola
(74) *Attorney, Agent, or Firm*—Birch, Stewart, Kolasch & Birch, LLP

(57) ABSTRACT

A 4-oxatricyclo[4.3.1.1$^{3,8}$]undecan-5-one derivative is shown by the following formula (1):

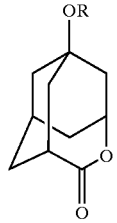

(1)

wherein R is a hydrogen atom or a (meth)acryloyl group, and carbon atoms constituting a ring may have a substituent in addition to the substituents indicated in the formula. This compound is a novel 4-oxatricyclo[4.3.1.1$^{3,8}$]undecan-5-one derivative having a hydroxyl group or a (meth)acryloyloxy group at the 1-position.

4 Claims, No Drawings

4-OXATRICYCLO[4.3.1.1 $^{3,8}$]UNDECAN-5-ONE DERIVATIVE AND PROCESS FOR PRODUCING THE SAME

BACKGROUND OF THE INVENTION

1. Field of the Invention

The present invention relates to 4-oxatricyclo[4.3.1.1$^{3,8}$] undecan-5-one derivatives which are useful as materials for photosensitive resins and other functional polymers and as materials for pharmaceuticals, agricultural chemicals, and other fine chemicals, and to a process for producing the derivative.

2. Description of the Related Art

A compound 4-oxatricyclo[4.3.1.1$^{3,8}$]undecan-5-one is known as an intermediate for organic synthesis (e.g., Synthesis, 1986, 741–743). This compound is obtained by introducing an oxygen atom to the adjacent position of a carbonyl group of 2-adamantanone. However, 4-oxatricyclo [4.3.1.1$^{3,8}$]undecan-5-one derivatives having a hydroxyl group or a (meth)acryloyloxy group bonded to a carbon atom at the 1-position are not known.

On the other hand, a lithography technique is used for the formation of fine patterns of semiconductor integrated circuits. The lithography technique includes the steps of covering a substrate having a thin film formed thereon (work) with a resist, subjecting the work to selective exposure to yield a latent image of a target pattern, subjecting the work to developing to form a patterned resist, dry-etching the work using the pattern as a mask, and then removing the resist to yield the target pattern. In the lithography technique, g-ray, i-ray, and other ultraviolet rays are used as light sources. However, with an increasing fineness of patterns, far ultraviolet rays, vacuum ultraviolet rays, excimer laser beams, electron beams, x-rays and other rays having a shorter wavelength are employed as the light sources. To form fine patterns using such a short-wavelength light source (e.g., ArF excimer laser), the resist used must have a satisfactory transparency at the wavelength of the light source, have a good adhesion to the substrate, be resistance to dry etching, and be satisfactorily soluble in a developer in development. As such resist materials, polymers of polymerizable monomers each having a bridged ring or a lactone ring have received attention in recent years (e.g., Japanese Unexamined Patent Application Publication No. 9-73173), but none of them sufficiently satisfies the above requirements.

SUMMARY OF THE INVENTION

Accordingly, an object of the invention is to provide a novel 4-oxatricyclo[4.3.1.1$^{3,8}$]undecan-5-one derivative having a hydroxyl group or a (meth)acryloyloxy group at the 1-position.

Another object of the invention is to provide a 4-oxatricyclo[4.3.1.1$^{3,8}$]undecan-5-one derivative which is useful as a monomeric material for photoresist resins.

A further object of the invention is to provide a process for efficiently producing the 4-oxatricyclo[4.3.1.1$^{3,8}$]undecan-5-one derivative.

After intensive investigations to achieve the above objects, the present inventors found that when a 4-adamantanone derivative having a hydroxyl group or a (meth)acryloyloxy group at the 1-position is oxidized with molecular oxygen by catalysis of an imide compound having a specific structure in the coexistence of a specific compound, a Baeyer-Villiger type reaction proceeds to efficiently yield a corresponding 4-oxatricyclo[4.3.1.1$^{3,8}$] undecan-5-one derivative. The present invention has been accomplished based on these findings.

Specifically, the invention provides, in an aspect, a 4-oxatricyclo[4.3.1.1$^{3,8}$]undecan-5-one derivative shown by the following formula (1):

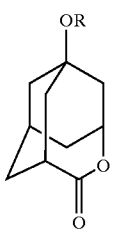

(1)

wherein R is a hydrogen atom or a (meth)acryloyl group, and carbon atoms constituting a ring may have a substituent in addition to the substituents indicated in the formula. Preferred R includes a (meth)acryloyl group.

In another aspect, the invention provides a process for producing a 4-oxatricyclo[4.3.1.1$^{3,8}$]undecan-5-one derivative. This process includes the step of oxidizing an adamantanone derivative shown by the following formula (2):

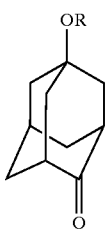

(2)

wherein R is a hydrogen atom or a (meth)acryloyl group, and carbon atoms constituting a ring may have a substituent in addition to the substituents indicated in the formula, with molecular oxygen in the presence of an imide compound shown by the following formula (3):

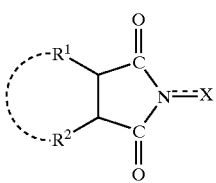

(3)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group; and one or two N-substituted cyclic imido groups indicated in the formula (3) may be further formed on the $R^1$, $R^2$, or on the double bond or aromatic or non-aromatic ring formed together by $R^1$ and $R^2$, and in the coexistence of an co-oxidizing agent to yield a 4-oxatricyclo[4.3.1.1$^{3,8}$]undecan-5-one derivative shown by the following formula (1):

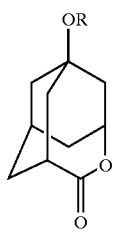

(1)

wherein R is a hydrogen atom or a (meth)acryloyl group, and carbon atoms constituting a ring may have a substituent in addition to the substituents indicated in the formula. The co-oxidizing agent includes, for example, a primary or secondary alcohol.

The invention provides, in a further aspect, a process for producing a 4-oxatricyclo[4.3.1.1$^{3,8}$]undecan-5-one derivative. This process includes the step of allowing a compound of the following formula (1a):

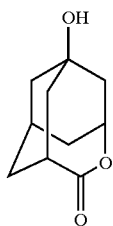

(1a)

wherein carbon atoms constituting a ring may have a substituent in addition to the substituents indicated in the formula, to react with (meth)acrylic acid or a reactive derivative thereof to yield a compound shown by the following formula (1b):

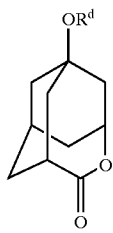

(1b)

wherein $R_d$ is a (meth)acryloyl group, and carbon atoms constituting a ring may have a substituent in addition to the substituents indicated in the formula.

In this specification, both acryloyl group and methacryloyl group are simply referred to as "(meth)acryloyl group".

DESCRIPTION OF THE PREFERRED EMBODIMENTS

In the 4-oxatricyclo[4.3.1.1$^{3,8}$]undecan-5-one derivative of the formula (1), R is a hydrogen atom or a (meth)acryloyl group. Carbon atoms constituting a ring may have a substituent in addition to the substituents (—OR group and oxo group) indicated in the formula. Such substituents include, but are not limited to, methyl group, ethyl group, isopropyl group, and other $C_1$–$C_4$ alkyl groups, hydroxyl group which may have a protective group, and carboxyl group which may have a protective group. As the protective groups, those conventionally used in the field of organic synthesis can be employed.

Typical 4-oxatricyclo[4.3.1.1$^{3,8}$]undecan-5-one derivatives of the formula (1) include, but are not limited to, 1-hydroxy-4-oxatricyclo[4.3.1.1$^{3,8}$]undecan-5-one, 1-(meth)acryloyloxy-4-oxatricyclo[4.3.1.1$^{3,8}$]undecan-5-one, 1-hydroxy-3,8-dimethyl-4-oxatricyclo[4.3.1.1$^{3,8}$]undecan-5-one, 1-(meth)acryloyloxy-3,8-dimethyl-4-oxatricyclo[4.3.1.1$^{3,8}$]undecan-5-one, 1-hydroxy-3,6-dimethyl-4-oxatricyclo[4.3.1.1$^{3,8}$]undecan-5-one, 1-(meth)acryloyloxy-3,6-dimethyl-4-oxatricyclo[4.3.1.1$^{3,8}$]undecan-5-one, 1,8-dihydroxy-4-oxatricyclo[4.3.1.1$^{3,8}$]undecan-5-one, 8-hydroxy-1-(meth)acryloyloxy-4-oxatricyclo[4.3.1.1$^{3,8}$]undecan-5-one, 1,6-dihydroxy-4-oxatricyclo[4.3.1.1$^{3,8}$]undecan-5-one, 6-hydroxy-1-(meth)acryloyloxy-4-oxatricyclo[4.3.1.1$^{3,8}$]undecan-5-one, 1,3-dihydroxy-4-oxatricyclo[4.3.1.1$^{3,8}$]undecan-5-one, 3-hydroxy-1-(meth)acryloyloxy-4-oxatricyclo[4.3.1.1$^{3,8}$]undecan-5-one, 8-carboxy-1-hydroxy-4-oxatricyclo[4.3.1.1$^{3,8}$]undecan-5-one, 8-carboxy-1-(meth)acryloyloxy-4-oxatricyclo[4.3.1.1$^{3,8}$]undecan-5-one, 6-carboxy-1-hydroxy-4-oxatricyclo[4.3.1.1$^{3,8}$]undecan-5-one, 6-carboxy-1-(meth)acryloyloxy-4-oxatricyclo[4.3.1.1$^{3,8}$]undecan-5-one, 3-carboxy-1-hydroxy-4-oxatricyclo[4.3.1.1$^{3,8}$]undecan-5-one, and 3-carboxy-1-(meth)acryloyloxy-4-oxatricyclo[4.3.1.1$^{3,8}$]undecan-5-one.

[Production of Compound of Formula (1)]

The 4-oxatricyclo[4.3.1.1$^{3,8}$]undecan-5-one derivative of the formula (1) can be obtained, for example, by oxidizing the adamantanone derivative of the formula (2) with molecular oxygen in the presence of the imide compound of the formula (3) and in the coexistence of a co-oxidizing agent. The term "co-oxidizing agent" used herein means and includes a compound which is oxidized together with the compound of the formula (2) under reaction conditions.

The substituents which carbon atoms constituting a ring may have in the formula (2) include the groups exemplified as substituents which carbon atoms constituting a ring may have in the formula (1).

Typical compounds of the formula (2) include, but are not limited to, 5-hydroxy-2-adamantanone, 5-(meth)acryloyloxy-2-adamantanone, 5-hydroxy-3,7-dimethyl-2-adamantanone, 5-(meth)acryloyloxy-3,7-dimethyl-2-adamantanone, 5-hydroxy-1,3-dimethyl-2-adamantanone, 5-(meth)acryloyloxy-1,3-dimethyl-2-adamantanone, 5,7-dihydroxy-2-adamantanone, 7-hydroxy-5-(meth)acryloyloxy-2-adamantanone, 1,5-dihydroxy-2-adamantanone, 1-hydroxy-5-(meth)acryloyloxy-2-adamantanone, 3,5-dihydroxy-2-adamantanone, 3-hydroxy-5-(meth)acryloyloxy-2-adamantanone, 7-carboxy-5-hydroxy-2-adamantanone, 7-carboxy-5-(meth)acryloyloxy-2-adamantanone, 1-carboxy-5-hydroxy-2-adamantanone, 1-carboxy-5-(meth)acryloyloxy-2-adamantanone, 3-carboxy-5-hydroxy-2-adamantanone, and 3-carboxy-5-(meth)acryloyloxy-2-adamantanone.

Of the substituents $R^1$ and $R^2$ in the imide compound of the formula (3), the halogen atom includes iodine, bromine, chlorine and fluorine atoms. The alkyl group includes, but is not limited to, methyl, ethyl, propyl, isopropyl, butyl, isobutyl, s-butyl, t-butyl, pentyl, hexyl, heptyl, octyl, decyl, and other straight- or branched-chain alkyl groups each having about 1 to 10 carbon atoms. Preferred alkyl groups are alkyl groups each having about 1 to 6 carbon atoms, of which lower alkyl groups each having about 1 to 4 carbon atoms are particularly preferred.

The aryl group includes phenyl, and naphthyl groups, for example. Illustrative cycloalkyl groups include cyclopentyl, and cyclohexyl groups. Illustrative alkoxy groups are methoxy, ethoxy, propoxy, isopropoxy, butoxy, isobutoxy, t-butoxy, pentyloxy, hexyloxy, and other alkoxy groups each having about 1 to 10 carbon atoms, and preferably having about 1 to 6 carbon atoms. Among them, lower alkoxy groups each having about 1 to 4 carbon atoms are especially preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. Preferred alkoxycarbonyl groups are alkoxycarbonyl groups each having about 1 to 6 carbon atoms in the alkoxy moiety, of which lower alkoxycarbonyl groups each having about 1 to 4 carbon atoms in the alkoxy moiety are particularly preferred.

The illustrative acyl groups include, for example, formyl, acetyl, propionyl, butyryl, isobutyryl, valeryl, isovaleryl, pivaloyl, and other acyl groups each having about 1 to 6 carbon atoms.

The substituents $R^1$ and $R^2$ may be identical to or different from each other. The substituents $R^1$ and $R^2$ in the formula (3) may be combined to form a double bond or an aromatic or non-aromatic ring. The preferred aromatic or non-aromatic ring has about 5 to 12 members, and particularly about 6 to 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring is composed of an aromatic ring in many cases. The ring may have a substituent. Such substituents include, but are not limited to, alkyl groups, haloalkyl groups, hydroxyl group, alkoxy groups, carboxyl group, alkoxycarbonyl groups, acyl groups, nitro group, cyano group, amino group, and halogen atoms.

In the formula (3), X represents an oxygen atom or a hydroxyl group, and the bond between the nitrogen atom N and X is a single bond or a double bond.

One or two N-substituted cyclic imido groups indicated in the formula (3) may be further formed on $R^1$, $R^2$, or on the double bond or aromatic or non-aromatic ring formed together by $R^1$ and $R^2$. For example, when $R^1$ or $R^2$ is an alkyl group having two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or non-aromatic ring, the N-substituted cyclic imido group may be formed with the adjacent two carbon atoms constituting the ring.

Preferred imide compounds include compounds of the following formulae:

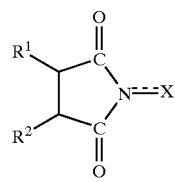
(3a)

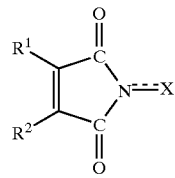
(3b)

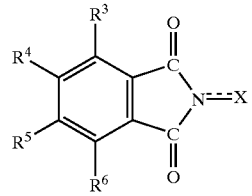
(3c)

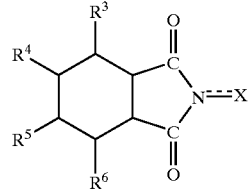
(3d)

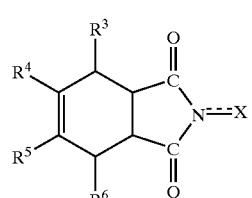
(3e)

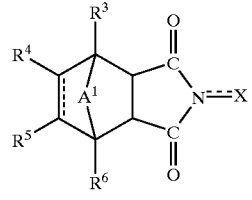
(3f)

wherein $R^3$ to $R^6$ are each, identical to or different from each other, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring; in the formula (3f), $A^1$ is a methylene group or an oxygen atom, and $R^1$ and $R^2$ have the same meanings as defined above, where one or two N-substituted cyclic imido groups indicated in the formula (3c) may be further formed on the benzene ring in the formula (3c); and X has the same meaning as defined above.

In the substituents $R^3$ to $R^6$, the alkyl group includes similar alkyl groups to those exemplified above, especially alkyl groups each having about 1 to 6 carbon atoms. The haloalkyl group includes trifluoromethyl group, and other haloalkyl groups each having about 1 to 4 carbon atoms, and the alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. The acyl group includes similar acyl groups to those described above, especially acyl groups each having about 1 to 6 carbon atoms. The illustrative halogen atoms include fluorine, chlorine and bromine atoms. Each of the substituents $R^3$ to $R^6$ is often a hydrogen atom, a lower alkyl group having about 1 to 4 carbon atoms, a carboxyl group, a nitro group, or a halogen atom. The ring formed together by $R^3$ to $R^6$ includes similar rings to the aforementioned rings which are formed together by $R^1$ and $R^2$. Among them, aromatic or non-aromatic 5- to 12-membered rings are particularly preferred.

Typically preferred imide compounds include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds can be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

Such acid anhydrides corresponding to the imide compounds of the formula (3) include, but are not limited to, succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred.

Each of the imide compounds of the formula (3) can be used alone or in combination in the oxidation reaction. The imide compounds can be used as being supported on a carrier. As such carriers, activated carbon, zeolite, silica, silica-alumina, bentonite, and other porous carries are frequently employed.

The proportion of the imide compound can be selected within a wide range and is, for example, about 0.0001 to 1 mole, preferably about 0.001 to 0.5 mole, more preferably about 0.01 to 0.4 mole, and often about 0.05 to 0.35 mole, relative to 1 mole of the compound of the formula (2).

In the inventive process, a promoter (co-catalyst) can be used in combination with the catalyst of the formula (3) to improve or enhance the rate and selectivity of the reaction. Such promoters include, but are not limited to, (i) compounds each having a carbonyl group combined with an electron attractive group, (ii) metallic compounds, and (iii) organic salts each composed of a polyatomic cation or a polyatomic anion and its counter ion, which polyatomic cation or anion contains a Group 15 or Group 16 element of the Periodic Table of Elements having at least one organic group bonded thereto. Each of these promoters can be used alone or in combination.

In the compounds (i) each having a carbonyl group combined with an electron attractive group, the electron attractive group includes, but is not limited to, phenyl; fluoromethyl, trifluoromethyl, tetrafluoroethyl, fluorophenyl, pentafluorophenyl, and other hydrocarbon groups each substituted with a fluorine atom. Practical examples of the compounds (i) include, for example, hexafluoroacetone, trifluoroacetic acid, pentafluorophenyl methyl ketoné, pentafluorophenyl trifluoromethyl ketone, and benzoic acid.

The use of these compounds can enhance the reaction rate of a Baeyer-Villiger type reaction. This is provably because these compounds are converted into highly reactive peroxides in a reaction system. The amount of the compound (i) is about 0.0001 to 1 mole, preferably about 0.01 to 0.7 mole, and more preferably about 0.05 to 0.5 mole, relative to 1 mole of the compound of the formula (2).

Metallic elements constituting the metallic compounds (ii) are not limited and can be any of metallic elements of the Groups 1 to 15 of the Periodic Table of Elements. The term "metallic element" as used herein also includes boron B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), and Group 15 elements (e.g., Sb, Bi). Preferred metallic elements include transition metal elements (elements of Groups 3 to 12 of the Periodic Table of Elements). Among them, elements of the Groups 5 to 11 of the Periodic Table of Elements are preferred, of which elements of Group 6, Group 7 and Group 9 are typically preferred. Especially, Mo, Co and Mn can be advantageously used. The valency of the metallic element is not particularly limited, and is about 0 to 6 in many cases.

The metallic compounds (ii) include, but are not limited to, elementary substances, hydroxides, oxides (including complex oxides), halides (fluorides, chlorides, bromides, and iodides), salts of oxoacids (e.g., nitrates, sulfates, phosphates, borates, and carbonates), oxoacids, isopolyacids, heteropolyacids, and other inorganic compounds of the aforementioned metallic elements; salts of organic acids (e.g., salts of acetic acid, propionic acid, hydrocyanic acid, naphthenic acid, or stearic acid), complexes, and other organic compounds of the metallic elements. Ligands for constituting the complexes include OH (hydroxo), alkoxy (e.g., methoxy, ethoxy, propoxy, and butoxy), acyl (e.g., acetyl and propionyl), alkoxycarbonyl groups (e.g., methoxycarbonyl and ethoxycarbonyl), acetylacetonato, cyclopentadienyl group, halogen atoms (e.g., chlorine, and bromine atoms), CO, CN, oxygen atom, $H_2O$ (aquo), phosphines (triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds. Each of the metallic compounds (ii) can be used alone or in combination.

The use of the metallic compounds (ii) improves the selectivity of the reaction in some cases. Particularly, the combination use of a compound containing V, Mo, Co, Mn or another transition metal element (excludingFe) with a compound containing a platinum group element (Ru, Rh, Pd, Os, Ir, or Pt) or Fe can markedly improve the selectivity to yield a target compound in a high yield. Especially, the combination use of a Co compound with Pt(dppb) ($\mu$-OH)]$_2(BH_4)_2$ or other platinum group metal-hydrogen complex compounds is preferred.

The proportion of the metallic compound (ii) is, for example, about 0.0001 to 0.7 mole, preferably about 0.001 to 0.5 mole, more preferably about 0.002 to 0.1 mole, and often about 0.005 to 0.05 mole, relative to 1 mole of the compound of the formula (2).

In the organic salts (iii), the Group 15 elements of the Periodic Table of Elements include N, P, As, Sb, and Bi, and the Group 16 elements of the Periodic Table of Elements include, for example, O, S, Se and Te. Preferred elements are N, P, As, Sb, and S, of which N, P, and S are typically preferred.

The organic groups to be bonded to atoms of the elements include, but are not limited to, hydrocarbon groups which may have a substituent, and substituted oxy groups. The hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having about 1 to 30 carbon atoms (preferably about 1 to 20 carbon atoms); cyclopentyl, cyclohexyl, and other alicyclic hydrocarbon groups each having about 3 to 8 carbon atoms; and phenyl, naphthyl, and other aromatic hydrocarbon groups each having about 6 to 14 carbon atoms. Substituents which the hydrocarbon groups may have include, but are not limited to, halogen atoms, oxo group, hydroxyl group, substituted oxy groups (e.g., alkoxy groups, aryloxy groups, and acyloxy groups), carboxyl group, substituted oxycarbonyl groups, substituted or unsubstituted carbamoyl groups, cyano group, nitro group, substituted or unsubstituted amino groups, alkylgroups (e.g., methyl, ethyl, and other $C_1$–$C_4$ alkyl groups), cycloalkyl groups, aryl groups (e.g., phenyl, and naphthyl groups), and heterocyclic groups. The preferred hydrocarbon groups include, for example, alkyl groups each having about 1 to 30 carbon atoms, and aromatic hydrocarbon groups (especially, phenyl or naphthyl group) each having about 6 to 14 carbon atoms. The substituted oxy groups include, but are not limited to, alkoxy groups, aryloxy groups and aralkyloxy groups.

The polyatomic cation is, for example, represented by the following formula (4). This polyatomic cation constitutes, with a counter anion, an organic onium salt represented by the following formula (5).

$$[R^a{}_m A]^+ \quad (4)$$

$$[R^a{}_m A]^- Y^- \quad (5)$$

In the above formulae, $R^a$ is a hydrocarbon group or a hydrogen atom. The four $R^a$s may be identical to or different from one another, and at least one $R^a$ is a hydrocarbon group. The atom A is an atom of Group 15 or Group 16 element of the Periodic Table of Elements. Two $R^a$s may be combined to form a ring with the adjacent A, or two $R^a$s may together form a double bond as one with the atom A and be concurrently combined with another $R^a$ to form a ring with the atom A. The numeral m denotes 3 or 4. $Y^-$ is a counter anion, and Y is an acid radical. The above hydrocarbon group may have, for example, any of the aforementioned substituents.

The rings which are to be formed by two $R^a$s with the adjacent A include, but are not limited to, pyrrolidine ring, piperidine ring, and other nitrogen-containing or phosphorus-containing heterocyclic rings each having about 3 to 8 members (preferably 5 or 6 members). Alternately, two $R^a$s may together form a double bond as one with the atom A and be concurrently combined with another $R^a$ to form a ring with the atom A. Such rings just mentioned above include pyridine ring, and other 5- to 8-membered nitrogen-containing heterocyclic rings. To these rings, a benzene ring or another ring may be condensed. Such a condensed ring includes, for example, quinoline ring. In many cases, m is 4 when A is an atom of Group 15 element of the Periodic Table of Elements, and, m is 3 when A is an atom of Group 16 element of the Periodic Table of Elements.

The atom A is preferably N, P, As, Sb or S, more preferably N, P or S, and particularly N or P. In the preferred polyatomic cations, all the four $R^a$s are organic groups (including cases where a ring containing A is formed).

The acid radical Y includes, but is not limited to, fluorine, chlorine, bromine, iodine, and other halogen atoms; nitrate radical ($NO_3$), sulfate radical ($SO_4$), phosphate radical ($PO_4$), perchlorate radical ($ClO_4$), and other inorganic acid radicals; acetate radical ($CH_3CO_2$), methanesulfonate radical, benzenesulfonate radical, and other organic acid radicals.

Preferred acid radicals include halogen atoms and inorganic acid radicals, of which chlorine atom, bromine atom and other halogen atoms are typically desirable.

Of the organic onium salts, organic ammonium salts, organic phosphonium salts, and organic sulfonium salts are typically preferred. Concrete examples of organic ammonium salts include tetramethylammonium chloride, tetraethylammonium chloride, tetrabutylammonium chloride, tetrahexylammonium chloride, trioctylmethylammonium chloride, triethylphenylammonium chloride, tributyl(hexadecyl)ammonium chloride, di(octadecyl) dimethylammonium chloride, and other quaternary ammonium chlorides, and corresponding quaternary ammonium bromides, and other quaternary ammonium salts each having four hydrocarbon groups bonded to its nitrogen atom; dimethylpiperidinium chloride, hexadecylpyridinium chloride, methylquinolinium chloride, and other cyclic quaternary ammonium salts.

Practical examples of the organic phosphonium salts include tetramethylphosphonium chloride, tetrabutylphosphonium chloride, tributyl(hexadecyl)phosphonium chloride, triethylphenylphosphonium chloride, and other quaternary phosphonium chlorides, and corresponding quaternary phosphonium bromides, and other quaternary phosphonium salts each having four hydrocarbon groups bonded to its phosphorus atom. Concrete examples of the organic sulfonium salts include triethylsulfonium iodide, ethyldiphenylsulfonium iodide, and other sulfonium salts each having three hydrocarbon groups bonded to its sulfur atom.

The polyatomic anion is represented by, for example, the following formula (6). This polyatomic anion constitutes, with a counter cation, an organic salt of the following formula (7).

$$[R^b AO_3]^{q-} \quad (6)$$

$$Z^{q+}[R^b AO_3]^{q-} \quad (7)$$

In the above formulae, $R^b$ is a hydrocarbon group or a hydrogen atom; A is an atom of Group 15 or Group 16 element of the Periodic Table of Elements; q denotes 1 or 2; and $Z^{q+}$ is a counter cation.

Such hydrocarbon groups represented by $R^b$ include, in addition to similar groups to the aforementioned hydrocarbon groups, resins (polymer chains or branched chains thereof). Preferred A includes, but is not limited to, S and P. The numeral q is 1 when A is S or the like, and q is 2 when A is P or the like. The atom Z includes, but is not limited to, sodium, potassium, and other alkali metals; magnesium, calcium, and other alkaline earth metals, of which alkali metals are preferred. The counter cation $Z^{q+}$ may be the above-mentioned polyatomic cation.

Illustrative organic salts of the formula (7) include methanesulfonates, ethanesulfonates, octanesulfonates, dodecanesulfonates, and other alkyl-sulfonates; benzenesulfonates, p-toluenesulfonates, naphthalenesulfonates, decylbenzenesulfonates, dodecylbenzenesulfonates, and other aryl-sulfonates which may be substituted with an alkyl group; sulfonic acid type ion exchange resins (ion exchangers); and phosphonic acid type ion exchange resins (ion exchangers). Of these salts, a $C_6$–$C_{18}$ alkyl-sulfonate, or a $C_6$–$C_{18}$ alkyl-aryl sulfonate is often used.

The proportion of the organic salt (iii) is, for example, about 0.0001 to 0.7 mole, preferably about 0.001 to 0.5 mole, more preferably about 0.002 to 0.1 mole, and often about 0.005 to 0.05 mole, relative to 1 mole of the compound of the formula (2). The use of the organic salt (iii) in excess amounts may reduce the reaction rate.

The molecular oxygen for use in oxidation includes, but is not limited to, pure oxygen, and oxygen diluted with an inert gas such as nitrogen, helium, argon, or carbon dioxide. Air is preferably used as the oxygen from the viewpoints of operating property and safety, as well as cost efficiency.

The amount of the molecular oxygen is generally equal to or more than 0.5 mole (e.g., equal to or more than 1 mole), preferably about 1 to 100 moles, and more preferably about 2 to 50 moles, relative to 1 mole of the compound of the formula (2). The molecular oxygen is often employed in excess moles relative to the compound of the formula (2).

In the above process, for example a primary or secondary alcohol can be used as a co-oxidizing agent. Such primary or secondary alcohols include a wide variety of alcohols, and may be any of monohydric, dihydric or polyhydric alcohols. The primary or secondary alcohol may have a variety of substituents. Such substituents include, but are not limited to, halogen atoms, oxo group, hydroxyl group, mercapto group, substituted oxy groups (e.g., alkoxy groups, aryloxy groups, and acyloxy groups), substituted thio groups, carboxyl group, substituted oxycarbonyl groups, substituted or unsubstituted carbamoyl groups, cyano group, nitro group, substituted or unsubstituted amino groups, alkyl groups, alkenyl groups, alkynyl groups, cycloalkyl groups, cycloalkenyl groups, aryl groups (e.g., phenyl and naphthyl groups), aralkyl groups, and heterocyclic groups.

Such primary alcohols include, but are not limited to, methanol, ethanol, 1-propanol, 1-butanol, 2-methyl-1-propanol, 1-pentanol, 1-hexanol, 1-octanol, 1-decanol, 1-hexadecanol, 2-buten-1-ol, ethylene glycol, trimethylene glycol, hexamethylene glycol, pentaerythritol, and other saturated or unsaturated aliphatic primary alcohols each having about 1 to 30 (preferably about 1 to 20, and more preferably about 1 to 15) carbon atoms; cyclopentylmethyl alcohol, cyclohexylmethyl alcohol, 2-cyclohexylethyl alcohol, and other saturated or unsaturated alicyclic primary alcohols; benzyl alcohol, 2-phenylethyl alcohol, 3-phenylpropyl alcohol, cinnamyl alcohol, and other aromatic primary alcohols; and 2-hydroxymethylpyridine, and other heterocyclic alcohols. Preferred primary alcohols include aliphatic primary alcohols such as saturated aliphatic primary alcohols each having about 1 to 20 carbon atoms.

Illustrative secondary alcohols include 2-propanol, s-butyl alcohol, 2-pentanol, 3-pentanol, 2-hexanol, 2-octanol, 4-decanol, 2-hexadecanol, 2-penten-4-ol, and other saturated or unsaturated aliphatic secondary alcohols each having about 3 to 30 (preferably about 3 to 20, and more preferably about 3 to 15) carbon atoms; cyclobutanol, cyclopentanol, cyclohexanol, cyclooctanol, cyclododecanol, cyclopentadecanol, 2-cyclohexen-1-ol, 3,5,5-trimethyl-2-cyclohexen-1-ol, 1,3-cyclohexanediol, 1,4-cyclohexanediol, 1,4-cyclooctanediol, 2,2-bis(4-hydroxycyclohexyl)propane, bis(4-hydroxycyclohexyl)methane, 4-(4-hydroxycyclohexyl)cyclohexanol, and other saturated or unsaturated alicyclic secondary alcohols each having about 3 to 20 members (preferably about 3 to 15 members, more preferably about 5 to 15 members, and especially about 5 to 8 members); 1-phenylethanol, 1-phenylpropanol, 1-phenylmethylethanol, diphenylmethanol (benzhydrol), and other aromatic secondary alcohols; and 1-(2-pyridyl) ethanol, and other heterocyclic secondary alcohols.

Preferred primary or secondary alcohols include secondary alcohols (e.g., s-butyl alcohol, and other aliphatic secondary alcohols; cyclohexanol and other alicyclic secondary alcohols; I-phenylethanol, diphenylmethanol (benzhydrol) and other aromatic secondary alcohols). Each of these alcohols can be used singly or in combination.

The primary or secondary alcohol as the co-oxidizing agent is generally converted into an aldehyde, a carboxylic acid, or a ketone upon reaction.

In the invented process, other compounds than primary or secondary alcohols can be employed as co-oxidizing agents. Such compounds include a variety of compounds that can be oxidizable with the imide compound and oxygen (refer to Japanese Unexamined Patent Application Publications No. 8-38909 and No. 9-327626). Such co-oxidizing agents other than primary or secondary alcohols include, for example, compounds each having a carbon-hydrogen bond at the adjacent position to an unsaturated bond (e.g., toluene, ethylbenzene, tetralin, fluorene, and other aromatic compounds each having a methyl group or methylene group at the adjacent position to an aromatic ring), compounds each having a methine carbon atom (e.g., decalin, adamantane, and other bridged cyclic compounds each having a methine group; and isobutane, and other chain or alicyclic hydrocarbons each having a methine carbon atom), cycloalkanes (e.g., cyclohexane), and non-aromatic heterocyclic compounds each having a carbon-hydrogen bond at the adjacent position to a hetero atom (e.g., chroman, and isochroman)

Each of these co-oxidizing agents can be used alone or in combination. The amount of the co-oxidizing agent is, for example, about 0.1 to 200 moles, preferably about 0.5 to 100 moles, more preferably about 1 to 50 moles, and especially about 2 to 30 moles, relative to 1 mole of the compound of the formula (2). The co-oxidizing agent can also serve as a reaction solvent.

In the above process, the role of the co-oxidizing agent is supposed to be as follows. The co-oxidizing agent (e.g., a primary or secondary alcohol) is oxidized to yield a compound (e.g., a peroxide when the co-oxidizing agent is a primary or secondary alcohol), and this compound is involved in a reaction in which the compound of the formula (2) is converted into a corresponding lactone [the compound of the formula (1)].

The oxidation reaction is generally performed in an organic solvent. Such organic solvents include, but are not limited to, acetic acid, propionic acid, and other organic acids; acetonitrile, propionitrile, benzonitrile, and other nitrites; formamide, acetamide, dimethylformamide (DMF), dimethylacetamide, andotheramides; hexane, octane, andother aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. In may cases, acetic acid and other organic acids, acetonitrile, benzonitrile, and other nitriles, trifluoromethylbenzene, and other halogenated hydrocarbons, ethyl acetate and other esters are used as the solvent.

A reaction temperature is, for example, about 0° C. to 300° C., preferably about 20° C. to 200° C., and more preferably about 30° C. to 150° C. The reaction is usually performed at a temperature of about 40° C. to 100° C. The reaction can be performed at atmospheric pressure or under a pressure (under a load). When the reaction is conducted under a pressure, the pressure is usually about 1 to 100 atm (e.g. 1.5 to 80 atm), and preferably about 2 to 70 atm. A reaction time can be appropriately selected within a range of, for example, about 30 minutes to 48 hours depending on the reaction temperature and pressure.

The reaction can be performed in a batch system, semi-batch system, continuous system or another conventional system, in the presence of, or under flow of, molecular oxygen.

After the completion of the reaction, reaction products can be easily separated and purified by a conventional technique such as filtration, concentration, distillation, extraction, crystallization, recrystallization, column chromatography and other separation means, or any combination of these separation means.

Alternatively, the compound of the formula (1) can be also obtained upon an ordinary Baeyer-Villiger reaction, i.e., a reaction of the compound of the formula (2) with hydrogen peroxide or another peroxide, or with m-chloroperbenzoic acid or another peracid.

Of the 4-oxatricyclo[4.3.1.1$^{3,8}$]undecan-5-one derivatives of the formula (1), a compound where R is an acryloyl group or methacryloyl group [the compound of the formula (1b)] can be obtained by allowing the compound of the formula (1a) to react with (meth)acrylic acid or a reactive derivative thereof. The compound of the formula (1a) is a compound (an alcohol derivative) where R is a hydrogen atom among the 4-oxatricyclo[4.3.1.1$^{3,8}$]undecan-5-one derivatives of the formula (1).

In the formulae (1a) and (1b), substituents which carbon atoms constituting the ring may have include the groups exemplified as substituents which carbon atoms consisting the ring in the formula (1) may have. Reactive derivatives of (meth)acrylic acid include, for example, acid halides, acid anhydrides, esters (e.g., $C_1$–$C_4$ alkyl esters, and active esters), and amides (e.g., active amides).

More practically, the compound of the formula (1b) can be obtained, for example, by the following process (i), (ii), or (iii). In the process (i), a compound (an alcohol derivative) where R is a hydrogen atom among the 4-oxatricyclo[4.3.1.1$^{3,8}$]undecan-5-one derivatives of the formula (1) is allowed to react with (meth)acrylic acid in the presence of an acid catalyst such as hydrochloric acid, sulfuric acid, or p-toluenesulfonic acid. In the process (ii), the alcohol derivative is allowed to react with a (meth) acrylic halide in the presence of a base such as triethylamine. In the process (iii), the alcohol derivative and a (meth) acrylic ester are subjected to transesterification in the presence of a transesterification catalyst. In the processes (i) and (ii), the reaction can be performed under usual esterification conditions. In the process (iii), the transesterification can be performed using a conventional transesterification catalyst such as sodium alkoxides, aluminium alkoxides, and titanates. However, a corresponding (meth)acryloyloxy derivative can be obtained in a high yield by using vinyl (meth) acrylate, propenyl (meth)acrylate, and another $C_2$–$C_4$ alkenyl (meth)acrylate as the (meth)acrylic ester and by using a compound of Group 3 element of the Periodic Table of Elements (e.g., samarium iodide, samarium triflate, samarium complexes, and other samarium compounds) as the transesterification catalyst.

[Production of Compound of Formula (2)]

Of the adamantanone derivatives of the formula (2) for use as materials in the process for producing the compound of the formula (1), a compound where R is a hydrogen atom can be obtained, for example, by the following process. Specifically, an adamantanone derivative shown by the following formula (8)

(8)

wherein R$^c$ is a hydrogen atom, and the other carbon atoms than carbon atoms to which the oxo group or R$^c$ indicated in the formula is bonded may have a substituent, is allowed to react with oxygen in the presence of the imide compound of the formula (3) and a vanadium compound and a manganese compound to yield an a damantanone derivative shown by the following formula (2a):

(2a)

wherein the other carbon atoms than carbon atoms to which the oxo group or hydroxyl group indicated in the formula may have a substituent.

In the formula (8), the other carbon atoms than carbon atoms to which the oxo group or R$^c$ indicated in the formula is bonded may have a substituent, and in the formula (2a), the other carbon atoms than carbon atoms to which the oxo group or hydroxyl group indicated in the formula may have a substituent. Such substituents include the groups exemplified as substituents which carbon atoms constituting the ring in the formula (1) may have.

Typical compounds of the formula (8) include, but are not limited to, 2-adamantanone, 3,7-dimethyl-2-adamantanone, 1,3-dimethyl-2-adamantanone, 7-hydroxy-2-adamantanone, 1-hydroxy-2-adamantanone, 7-carboxy-2-adamantanone, and 1-carboxy-2-adamantanone.

The compound of the formula (8) can be obtained, for example, by allowing a corresponding adamantane derivative to react with oxygen in. the presence of the imide compound of the formula (3), the metallic compound, and a strong acid (e.g., a concentrated sulfuric acid) to convert the adamantane derivative into an oxo derivative (refer to Japanese Unexamined Patent Application Publication No. 10-309469).

The proportion of the imide compound in the production of the adamantanone derivative of the formula (2a) can be selected within a wide range and is, for example, about 0.0001 to 1 mole, preferably about 0.001 to 0.5 mole, more preferably about 0.01 to 0.4 mole, and often about 0.05 to 0.35 mole, relative to 1 mole of the compound of the formula (8).

As the vanadium compound and manganese compound, a wide variety of compounds each containing a vanadium atom or a manganese atom can be employed. Each of these vanadium compounds and manganese compounds can be respectively used alone or in combination. The vanadium element in the vanadium compound has a valency of 2 to 5, and the manganese element in the manganese compound has a valency of 1 to 7.

Such vanadium compounds and manganese compounds include, but are not limited to, hydroxides, oxides (including complex oxides), halides (fluorides, chlorides, bromides, and iodides), salts of oxoacids (e.g., nirates, sulfates, phosphates, borates, and carbonates), oxoacids, isopolyacids, heteropolyacids, and other inorganic compounds of each element; salts of organic acids (e.g., salts of acetic acid, propionic acid, hydrocyanic acid, naphthenic acid, or stearic acid), complexes, and other organic compounds of each element. Ligands constituting the complexes include OH (hydroxo), alkoxy (e.g., methoxy, ethoxy, propoxy, andbutoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (e.g., triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Illustrative vanadium compounds include vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valency of 2 to 5. Typical manganese compounds include, but are not limited to, manganese hydroxide, manganese oxide, manganese chloride, manganese bromide, manganese nitrate, manganese sulfate, manganese phosphate, and other inorganic compounds; manganese acetate, manganese naphthenate, manganese stearate, and other salts of organic acids; and acetylacetonatomanganese, and other complexes, and other divalent or trivalent manganese compounds.

The total amount of the vanadium compound and the manganese compound is, for example, about 0.0001 to 0.7 mole, preferably about 0.001 to 0.5 mole, more preferably about 0.0015 to 0.1 mole, and often about 0.0015 to 0.05 mole (particularly, about 0.002 to 0.01 mole), relative to 1 mole of the compound of the formula (8).

The ratio (metallic atomic ratio) of the vanadium compound to the manganese compound is, for example, such that the former/the latter is about 99/1 to 1/99, preferably about 95/5 to 10/90, more preferably about 90/10 to 30/70, and often about 80/20 to 50/50.

The other metallic catalysts can be employed as co-catalysts in combination with the above compounds within a range not deteriorating the rate and selectivity of the reaction.

As the oxygen, either of molecular oxygen and nascent oxygen can be used. Such molecular oxygen includes, but is not limited to, pure oxygen, and oxygen diluted with an inert gas such as nitrogen, helium, argon or carbon dioxide. Air is preferably used as the oxygen from the viewpoints of operating property and safety, as well as cost efficiency.

The amount of the oxygen is, generally, equal to or more than about 0.5 mole (e.g., equal to or more than 1 mole), preferably about 1 to 100 moles, and more preferably about 2 to 50 moles, relative to 1 mole of the compound of the formula (8). The oxygen is often used in excess moles relative to the compound of the formula (8).

The reaction is generally performed in an organic solvent. The type of the organic solvent, reaction temperature, reaction pressure, and other reaction conditions are the same with the conditions described in the process for producing the compound of the formula (1) from the compound of the formula (2). The reaction can be performed in a batch system, semi-batch system, continuous system or another conventional system in the presence of, or under flow of oxygen. This process can introduce a hydroxyl group into a specific position of an adamantane ring to yield the compound of the formula (2a) in a high yield. After the completion of the reaction, reaction products can be easily separated and purified by a conventional technique such as filtration, concentration, distillation, extraction, crystallization, recrystallization, column chromatography, and other separation means, or any combination of these separation means.

Of the adamantanone derivatives of the formula (2), a compound where R is a (meth)acryloyl group c an b e produced, using the compound of the formula (2a), in accordance with any of the processes for producing the compound of the formula (1b) from the compound of the formula (1a) (e.g., the processes (i) (ii), and (iii)). The compound of the formula (1a) is a compound where R is a hydrogen atom among the compounds of the formula (1), and the compound of the formula (1b) is a compound where R is an acryloyl group or methacryloyl group among the compounds of the formula (1).

The invented 4-oxatricyclo[4.3.1.1$^{3,8}$]undecan-5-one derivatives of the formula (1) are useful as materials for photosensitive resins, and other functional polymers, and as materials for pharmaceuticals, agricultural chemicals, and other fine chemicals. Among them, when a compound where R is a (meth)acryloyl group is used as a monomeric component of a resist resin, the adamantane skeleton exhibits a higher dry etching resistance. In addition, this compound has a highly hydrophilic lactone ring and has a satisfactory solubility and a high adhesion to a substrate. Specifically, the compound in question is an ideal compound that can satisfy three requirements, i.e., dry etching resistance, solubility, and adhesion in one molecule.

As thus described, the invention can provide novel 4-oxatricyclo[4.3.1.1$^{3,8}$]undecan-5-one derivatives each having a hydroxyl group or (meth)acryloyloxy group at the 1-position, and a process for efficiently producing the derivatives. These compounds are useful, for example, as materials for photosensitive resins such as acid-sensitive polymers constituting photoresist resin compositions and as materials for fine chemicals.

The present invention will be illustrated in further detail with reference to several examples below, which are not intended to limit the scope of the invention.

PRODUCTION EXAMPLE 1

A mixture of 0.1 mol of 2-adamantanone, 10 mmol of N-hydroxyphthalimide, 0.33 mmol of acetylacetonatovanadium V $(AA)_3$, 0.17 mmol of acetylacetonatomanganese $Mn(AA)_3$, and 250 ml of acetic acid was stirred at 85° C. in an oxygen atmosphere (1 atm) for 10 hours. The resulting reaction mixture was concentrated and was then extracted with ethyl acetate. A portion of an organic layer was concentrated and was then cooled for crystallization to yield 5-hydroxy-2-adamantanone of the following formula in a yield of 48% with a conversion rate from 2-adamantanone of 74%.

[Spectrum Data of 5-Hydroxy-2-adamantanone]

IR $(cm^{-1})$: 3410, 2920, 2810, 1720, 1440, 1330, 1240, 1060, 880

MS m/e: 166 ($[M^+]$), 148, 119

EXAMPLE 1

A mixture of 100 mmol of 5-hydroxy-2-adamantanone, 200 mmol of benzhydrol, 10 mmol of N-hydroxyphthalimide, 0.1 mmol of cobalt(II) acetate, and 200 ml of benzonitrile was stirred at 75° C. in an oxygen atmosphere (1 atm) for 6 hours. A reaction mixture was concentrated and was then subjected to column chromatography on a silica gel to yield 1-hydroxy-4-oxatricyclo[4.3.1.1$^{3,8}$]undecan-5-one of the following formula in a yield of 48% with a conversion rate from 5-hydroxy-2-adamantanone of 67%.

[Spectrum Data of 1-Hydroxy-4-oxatricyclo[(4.3.1.1$^{3,8}$]undecan-5-one]

MS m/e: 182 ($[M^+]$), 138, 120

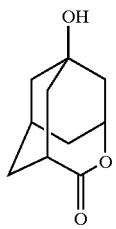

EXAMPLE 2

A mixture of 50 mmol of 1-hydroxy-4-oxatricyclo[4.3.1.1$^{3,8}$]undecan-5-one, 150 mmol of acryloyl chloride, 150 mmol of triethylamine, and 250 ml of toluene was stirred at 60° C. for 4 hours. The resulting reaction mixture was concentrated and was then subjected to column chromatography on a silica gel to yield 1-acryloyloxy-4-oxatricyclo[4.3.1.1$^{3,8}$]undecan-5-one of the following formula in a yield of 50% with a conversion rate from 1-hydroxy-4-oxatricyclo[4.3.1.1$^{3,8}$]undecan-5-one of 73%.

[Spectrum Data of Acryloyloxy-4-oxatricyclo[4.3.1.1$^{3,8}$]undecan-5-one]

MS m/e: 236 ($[M^+]$), 192, 120

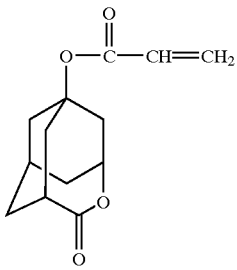

Other embodiments and variations will be obvious to those skilled in the art, and this invention is not to be limited to the specific matters stated above.

What is claimed is:

1. A 4-oxatricyclo[4.3.1.1$^{3,8}$]undecan-5-one derivative shown by the following formula (1):

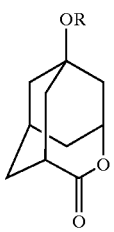

(1)

wherein R is a (meth)acryloyl group and the ring structure is optionally substituted.

2. A process for producing a 4-oxatricyclo[4.3.1.1$^{3,8}$]undecan-5-one derivative, comprising the step of oxidizing an adamantanone derivative shown by the following formula (2):

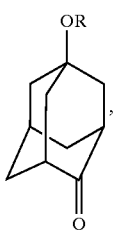

(2)

wherein R is a hydrogen atom or a (meth)acryloyl group and the ring structure is optionally substituted, with molecular oxygen in the presence of an imide compound shown by the following formula (3):

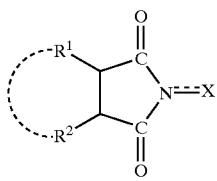

(3)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group; and one or two N-substituted cyclic imido groups indicated in the formula (3) may be further formed on said $R^1$, $R^2$, or on the double bond or aromatic or non-aromatic ring formed together by $R^1$ and $R^2$, and in the coexistence of an co-oxidizing agent to yield a 4-oxatricyclo[$4.3.1.1^{3,8}$]undecan-5-one derivative shown by the following formula (1):

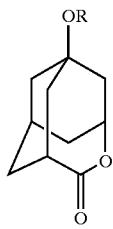

(1)

wherein R is a hydrogen atom or a (meth)acryloyl group and the ring structure is optionally substituted.

3. The process according to claim 2, wherein said co-oxidizing agent is a primary or secondary alcohol.

4. A process for producing a 4-oxatricyclo[$4.3.1.1^{3,8}$]undecan-5-one derivative, comprising the step of allowing a compound of the following formula (1a):

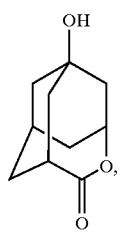

(1a)

wherein the ring structure is optionally substituted, to react with (meth)acrylic acid or a reactive derivative thereof to yield a compound shown by the following formula (1b):

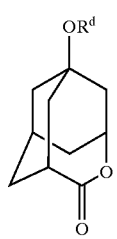

(1b)

wherein $R^d$ is a (meth)acryloyl group and the ring structure is optionally substituted.

* * * * *